United States Patent
Tang

(10) Patent No.: US 9,302,650 B2
(45) Date of Patent: Apr. 5, 2016

(54) VEHICLE BURGLARPROOF SYSTEM AND VEHICLE BURGLARPROOF METHOD

(71) Applicant: Wistron Corporation, New Taipei (TW)

(72) Inventor: Jen-Sheng Tang, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 0 days.

(21) Appl. No.: 14/551,281

(22) Filed: Nov. 24, 2014

(65) Prior Publication Data
US 2015/0258963 A1  Sep. 17, 2015

(30) Foreign Application Priority Data
Mar. 14, 2014 (TW) .............................. 103109340 A

(51) Int. Cl.
*B60R 25/25* (2013.01)
*B60R 25/30* (2013.01)
*A61B 5/117* (2006.01)
*A61B 5/0402* (2006.01)
*A61B 5/00* (2006.01)
*A61B 5/04* (2006.01)

(52) U.S. Cl.
CPC ............... *B60R 25/25* (2013.01); *A61B 5/0402* (2013.01); *A61B 5/117* (2013.01); *A61B 5/6893* (2013.01); *B60R 25/30* (2013.01); *A61B 5/04012* (2013.01)

(58) Field of Classification Search
CPC ........ B60R 25/25; B60R 25/30; A61B 5/117; A61B 5/0402; A61B 5/04012
USPC .......................................................... 701/2
See application file for complete search history.

(56) References Cited

U.S. PATENT DOCUMENTS

| | | | |
|---|---|---|---|
| 7,034,654 B2 | 4/2006 | Forest et al. | |
| 2008/0252412 A1* | 10/2008 | Larsson | B60R 25/25 340/5.2 |
| 2012/0101690 A1 | 4/2012 | Srinivasan et al. | |
| 2013/0096733 A1* | 4/2013 | Manotas, Jr. | F02N 11/0807 701/2 |
| 2013/0307670 A1* | 11/2013 | Ramaci | G05B 1/00 340/5.82 |

(Continued)

FOREIGN PATENT DOCUMENTS

CN           102469948 A        5/2012

OTHER PUBLICATIONS

"Car Access"; http://www.atmel.com/applications/automotive/car_access/default.aspx; © 2014 Atmel Corporation.

(Continued)

*Primary Examiner* — Fadey Jabr
*Assistant Examiner* — Yazan A Soofi
(74) *Attorney, Agent, or Firm* — McClure, Qualey & Rodack, LLP

(57) ABSTRACT

A vehicle burglarproof system and a vehicle burglarproof method are disclosed. The vehicle burglarproof system comprises a vehicle component, an electrocardiography (ECG) sensor, a first register, a remote controller and a microcontroller. The remote controller comprises a second register. The ECG sensor senses current ECG information. The first register stores the current ECG information. The second register stores pre-recorded ECG information. If the current ECG information matches the pre-recorded ECG information, the microcontroller controls the vehicle component to change to a second state from a first state which is different from the second state.

20 Claims, 5 Drawing Sheets

(56) References Cited

U.S. PATENT DOCUMENTS

| | | | |
|---|---|---|---|
| 2014/0070917 A1* | 3/2014 | Protopapas | B60R 25/30 340/3.1 |
| 2014/0282877 A1* | 9/2014 | Mahaffey | H04L 63/0853 726/3 |
| 2014/0285319 A1* | 9/2014 | Khan | G07C 9/00309 340/5.61 |

OTHER PUBLICATIONS

"Engine Immobilizer"; http://www.vehicle-lab.net/immobilizer.html ; Copyright © 2007 N. Eyal & Co.
TW Office Action dated Sep. 8, 2015 in corresponding Taiwan application (No. 103109340).
Partial English translation of TW Office Action dated Sep. 8, 2015 in corresponding Taiwan application (No. 103109340).

* cited by examiner

VEHICLE BURGLARPROOF SYSTEM AND VEHICLE BURGLARPROOF METHOD

This application claims the benefit of Taiwan application Ser. No. 103109340, filed Mar. 14, 2014, the subject matter of which is incorporated herein by reference.

BACKGROUND OF THE INVENTION

1. Field of the Invention

The invention relates in general to a burglarproof device, and more particularly to a vehicle burglarproof system and a vehicle burglarproof method.

2. Description of the Related Art

Most of early burglarproof devices used in vehicles are mechanic burglarproof devices which incapacitate the mechanisms or control devices of the vehicles by using mechanic locks. Along with the rapid advance in technology, electronic burglarproof devices incorporated with computer and electronic technology start to be used in vehicles. Electronic burglarproof devices provide burglarproof function through key chips. A conventional electronic burglarproof device recognizes the owner of a vehicle according to a key chip, hence effectively reducing occurrences of vehicle theft. Once the vehicle owner misplaced his/her key chip, anyone who holds the key chip can unlock the vehicle and start the engine.

SUMMARY OF THE INVENTION

The invention is directed to a vehicle burglarproof system and a vehicle burglarproof method capable of recognizing the owner of a vehicle according to his/her ECG information, hence effectively reducing occurrences of vehicle theft accompanied with the misplacement of key chip.

According to one embodiment of the present invention, a vehicle burglarproof system is disclosed. The vehicle burglarproof system comprises a vehicle component, an electrocardiography (ECG) sensor, a first register, a remote controller and a microcontroller. The remote controller comprises a second register. The ECG sensor senses current ECG information. The first register stores the current ECG information. The second register stores pre-recorded ECG information. If the current ECG information matches the pre-recorded ECG information, the microcontroller controls the vehicle component to change to a second state from a first state which is different from the second state.

According to another embodiment of the present invention, a vehicle burglarproof method is disclosed. The vehicle burglarproof method comprises: sensing current ECG information; determining whether the current ECG information matches a pre-recorded ECG information stored in a remote controller; controlling the vehicle component to change to a second state from a first state if the current ECG information matches the pre-recorded ECG information, wherein the first state is different from the second state.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
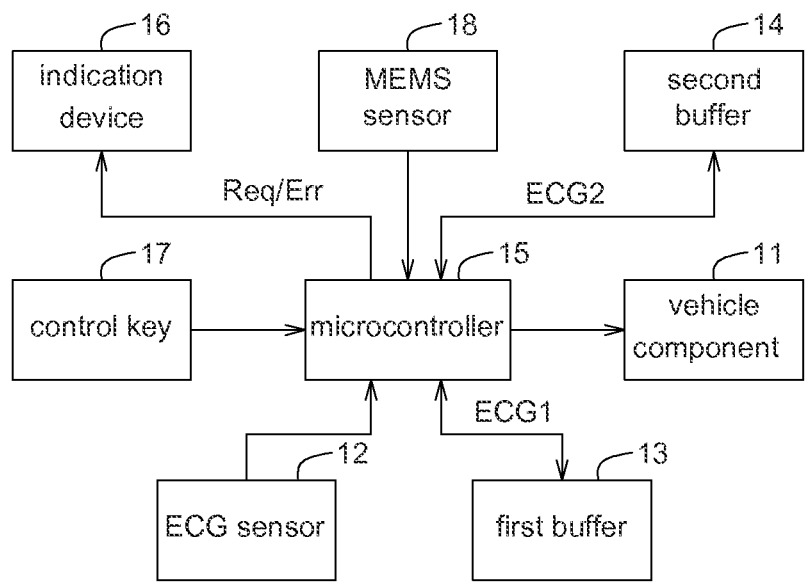
FIG. 1 is a schematic diagram of a vehicle burglarproof system.
Figure 2:
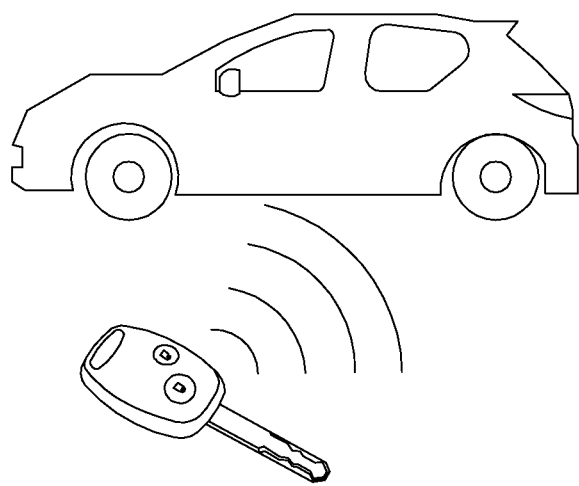
FIG. 2 is a schematic diagram of is a vehicle and a remote controller.

Refer to FIG. 1 and FIG. 2 at the same time. FIG. 1 is a schematic diagram of a vehicle burglarproof system. FIG. 2 is a schematic diagram of is a vehicle and a remote controller. The vehicle burglarproof system 1 comprises a vehicle component 11, an electrocardiography (ECG) sensor 12, a first register 13, a second register 14, a microcontroller 15, an indication device 16, a control key 17 and an MEMS sensor 18. The ECG sensor 12 senses a current ECG information ECG1. The first register 13 stores the current ECG information ECG1. The second register 14 is disposed on the remote controller 2 and stores pre-recorded ECG information ECG2. The current ECG information ECG1 and the pre-recorded ECG information ECG2 comprises PQRST wave of the ECG.

The microcontroller 15 determines whether the current ECG information ECG1 matches the pre-recorded ECG information ECG2. If the current ECG information ECG1 matches the pre-recorded ECG information ECG2, the microcontroller 15 controls the vehicle component 11 to change to a second state from a first state which is different from the second state. The indication device 16 indicates that the user senses the current ECG information ECG1. The indication device 16 can be realized by such as an LED or a dashboard. For example, after the user activates the control key 17, the microcontroller 15 determines whether the current ECG information ECG1 stored in the first register 13 exists. If the current ECG information ECG1 does not exist, the microcontroller 15 outputs a current ECG information request Req to the indication device 16 to request the user to contact the ECG sensor 12. If the current ECG information ECG1 does not match the pre-recorded ECG information ECG2, the microcontroller 15 outputs an error message Err to the indication device 16 and determines whether the current ECG information ECG1 needs to be verified once again. Based on the error message Err provided by the indication device 16, the user knows whether the current ECG information ECG1 needs to be sensed once again. The MEMS sensor 18 senses whether the remote controller 2 leaves the user.

First Embodiment

Figure 3:
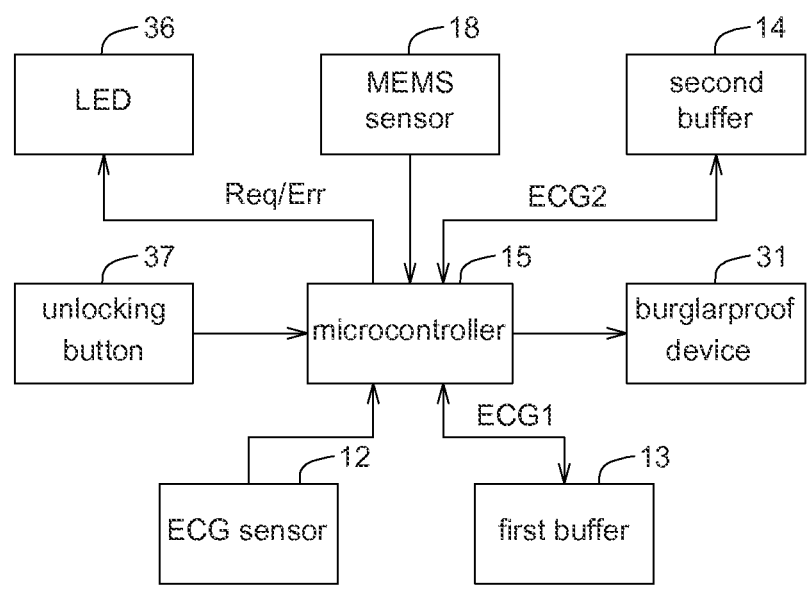
FIG. 3 is a block diagram of a vehicle burglarproof system is a according to the first embodiment.
Figure 4:
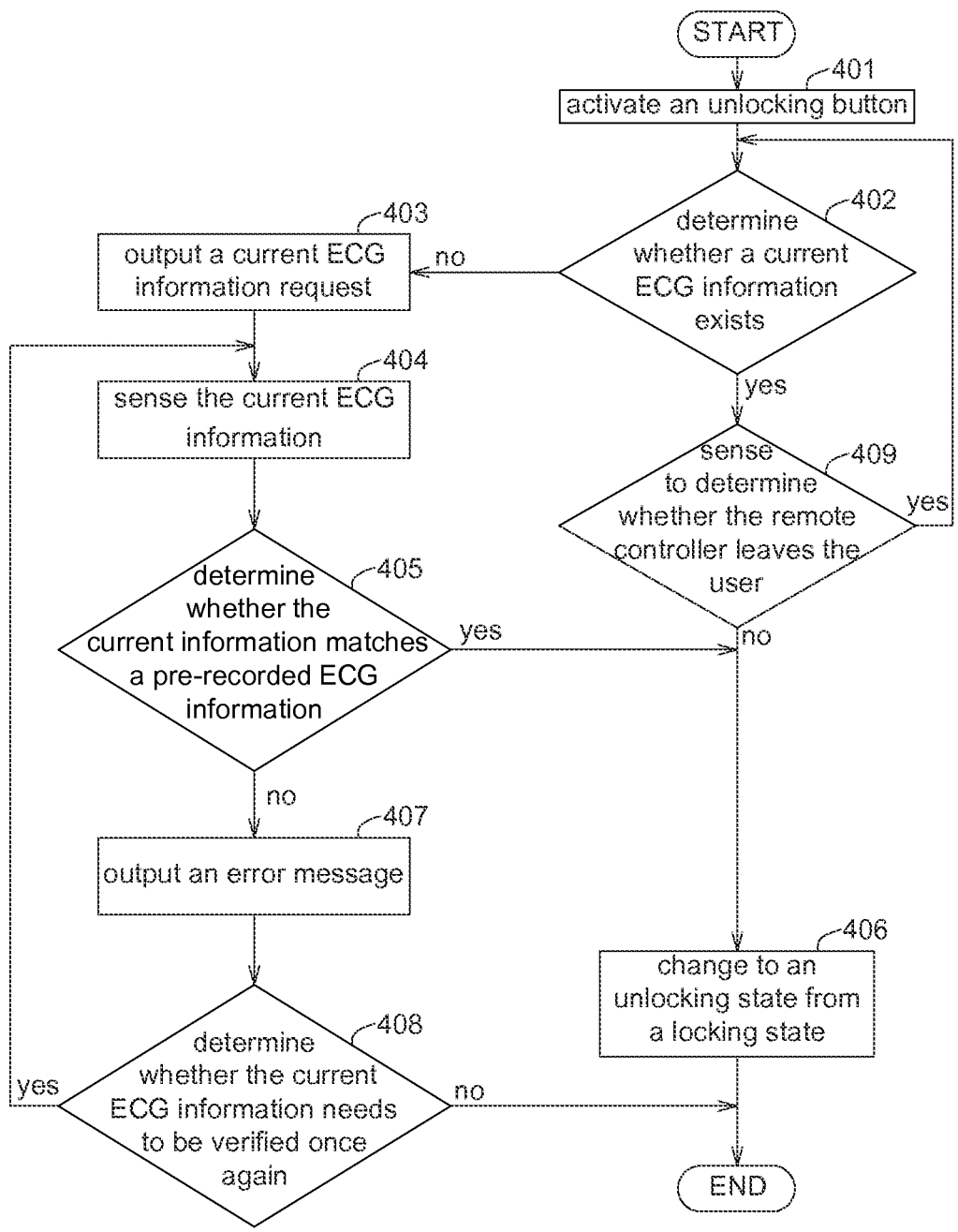
FIG. 4 is a flowchart of a vehicle burglarproof method according to a first embodiment.

Refer to FIG. 2, FIG. 3 and FIG. 4 at the same time. FIG. 3 is a block diagram of a vehicle burglarproof system is a according to the first embodiment. FIG. 4 is a flowchart of a vehicle burglarproof method according to a first embodiment. In the present embodiment, the vehicle component, the indication device and the control key of the vehicle burglarproof system 3 are respectively exemplified by a burglarproof device 31, an LED 36 and an unlocking button 37, and the first state and the second state are respectively exemplified by a locking state and an unlocking state. The LED 36 and the unlocking button 37 can be disposed in the remote controller 2.

The vehicle burglarproof method can be used in the vehicle burglarproof system 3, and comprises following steps. Firstly, the method begins at step 401, the user activates the unlocking button 37. Next, the method proceeds to step 402, the microcontroller 15 determines whether a current ECG information ECG1 stored in the first register 13 exists. If the current ECG information ECG1 does not exist, the method proceeds to step 403. In step 403, the microcontroller 15 outputs a current ECG information request Req to the LED 36 to request the user to contact the ECG sensor 12. Then, the method proceeds to step 404, the ECG sensor 12 senses the current ECG information ECG1. Then, the method proceeds to step 405, the microcontroller 15 determines whether the current ECG information ECG1 matches a pre-recorded ECG information ECG2. If the current ECG information ECG1 matches the pre-recorded ECG information ECG2, the method proceeds to step 406. In step 406, the microcontroller 15 controls the burglarproof device 31 to change to the unlocking state from the locking state. Conversely, if the current ECG information ECG1 does not match the pre-recorded ECG information ECG2, the method proceeds to step 407. In step 407, the microcontroller 15 outputs an error message Err to LED 36 to request the user to contact the ECG sensor 12. In step 408, the microcontroller 15 determines whether the current ECG information ECG1 needs to be verified once again. If the user contacts the ECG sensor 12, this implies that the current ECG information ECG1 needs to be verified once again, and the method proceeds to step 404. Conversely, if the user does not contact the ECG sensor 12, this implies that the current ECG information ECG1 does not need to be verified once again, and the vehicle burglarproof method terminates.

If the current ECG information ECG1 exists, the method proceeds to step 409. In step 409, the MEMS sensor 18 senses and determines whether the remote controller 2 leaves the user. If the remote controller 2 does not leave the user, the method proceeds to step 406. In step 406, the microcontroller 15 controls the burglarproof device 31 to change to the unlocking state from the locking state. Conversely, if the remote controller 2 leaves the user, the method once again executes step 402 to assure safety of use.

Furthermore, the microcontroller 15 can use the MEMS sensor 18 to determine whether a resting time of the remote controller 2 is shorter than a pre-determined time so as to determine whether the remote controller 2 leaves the user. If the resting time of the remote controller 2 is shorter than the pre-determined time, this implies that the remote controller 2 does not leave the user, and the microcontroller 15 controls the burglarproof device 31 to change to the unlocking state from the locking state. Conversely, if the resting time of the remote controller 2 is not shorter than the pre-determined time, this implies that the remote controller 2 leaves the user, and step 402 needs to be executed once again to assure the safety of use.

Second Embodiment

Figure 5:
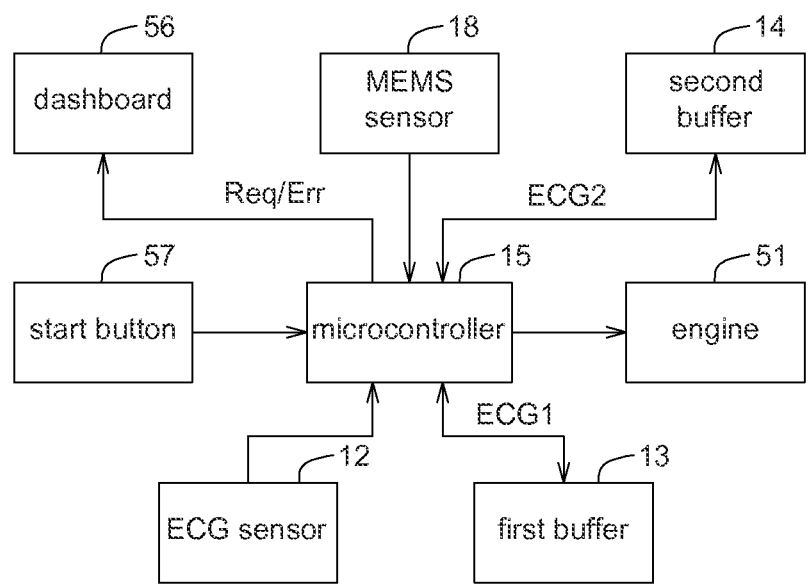
FIG. 5 is a block diagram of a vehicle burglarproof system according to the second embodiment.
Figure 6:
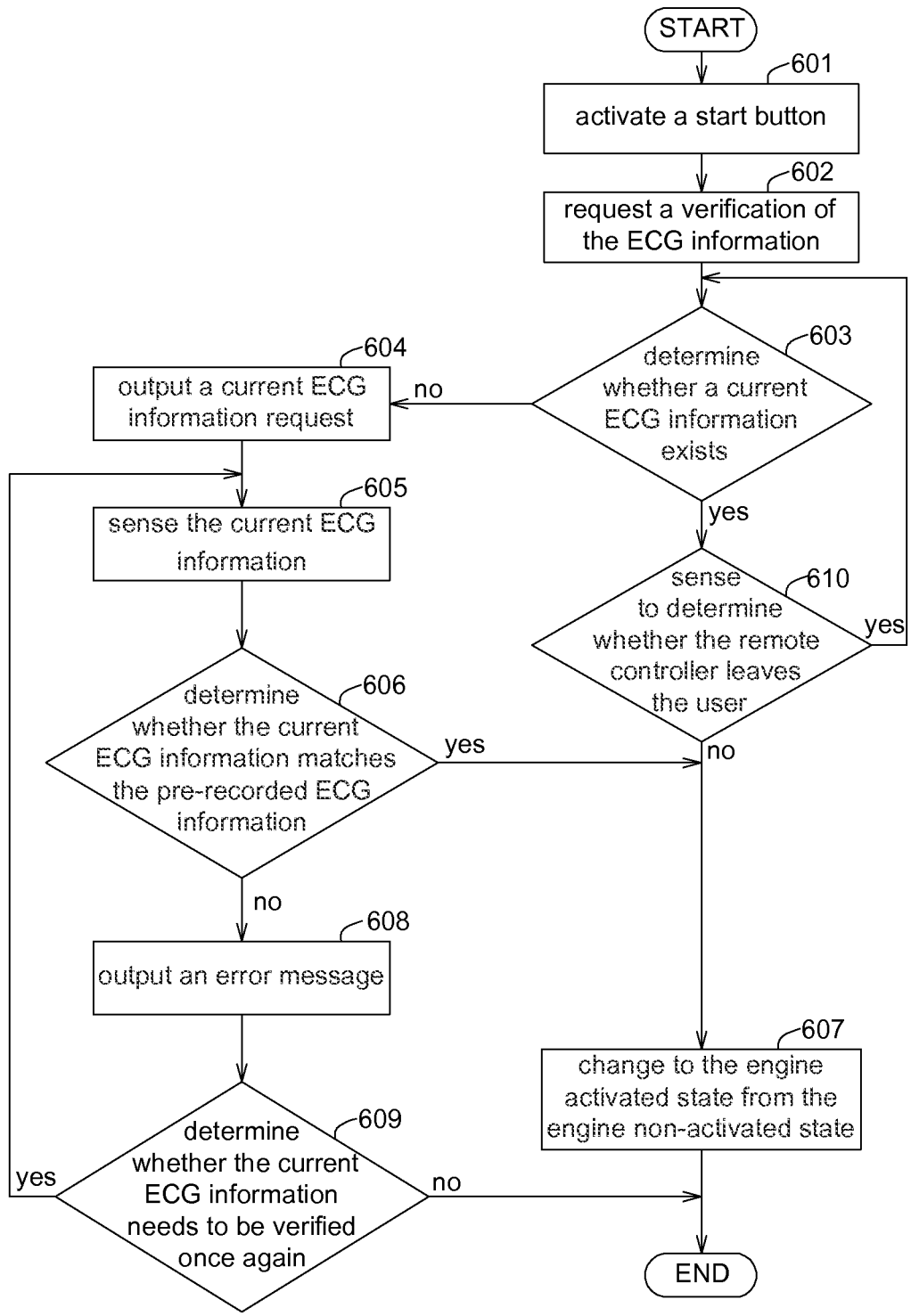
FIG. 6 is a flowchart of a vehicle burglarproof method according to the second embodiment.

Refer to FIG. 2, FIG. 5 and FIG. 6 at the same time. FIG. 5 is a block diagram of a vehicle burglarproof system according to the second embodiment. FIG. 6 is a flowchart of a vehicle burglarproof method according to the second embodiment. In the present embodiment, the vehicle component, the indication device and the control key of the vehicle burglarproof system 5 are respectively exemplified by an engine 51, a dashboard 56 and a start button 57, and the first state and the second state are respectively exemplified by an engine non-activated state and an engine activated state.

The vehicle burglarproof method can be used in a vehicle burglarproof system 5, and comprises following steps. Firstly, the method begins at step 601, the user activates the start button 57. Next, the method proceeds to step 602, the microcontroller 15 requests a verification of the ECG information. Then, the method proceeds to step 603, the microcontroller 15 determines whether a current ECG information ECG1 stored in the first register 13 exists. If the current ECG information ECG1 does not exist, the method proceeds to step 604. In step 604, the microcontroller 15 outputs a current ECG information request Req to the dashboard 56 to request the user to contact the ECG sensor 12.

Then, the method proceeds to step 605, the ECG sensor 12 senses the current ECG information ECG1. Then, the method proceeds to step 606, the microcontroller 15 determines whether the current ECG information ECG1 matches the pre-recorded ECG information ECG2. If the current ECG information ECG1 matches the pre-recorded ECG information ECG2, the method proceeds to step 607. In step 607, the microcontroller 15 controls the engine 51 to change to the engine activated state from the engine non-activated state. Conversely, if the current ECG information ECG1 does not match the pre-recorded ECG information ECG2, the method proceeds to step 608. In step 608, the microcontroller 15 outputs an error message Err to the dashboard 56 to request the user to contact the ECG sensor 12. Then, the method proceeds to step 609, the microcontroller 15 determines whether the current ECG information ECG1 needs to be verified once again. If the user contacts the ECG sensor 12, this implies that the current ECG information ECG1 needs to be verified once again and step 605 is executed once again. Conversely, if the user does not contact the ECG sensor 12, this implies that the current ECG information ECG1 does not need to be verified once again, and the vehicle burglarproof method terminates.

If the current ECG information ECG1 exists, the method proceeds to step 610. In step 610, the MEMS sensor 18 senses to determine whether the remote controller 2 leaves the user. If the remote controller 2 does not leave the user, the method proceeds to step 607. In step 607, the microcontroller 15 controls the engine 51 to change to the engine activated state from the engine non-activated state. Conversely, if the remote controller 2 leaves the user, step 603 is executed once again to assure the safety of use.

The vehicle burglarproof system and the vehicle burglarproof method disclosed in above embodiments verify a vehicle owner's identity according to his/her ECG information. Therefore, even if the owner misplaced his/her key chip, the burglar cannot steal the vehicle with the misplaced key chip. In addition, if the remote controller does not leave the owner, the owner can quickly unlock or activate the engine with the remote controller in lieu of the key chip. Thus, the operation of the vehicle is made more convenient.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A vehicle burglarproof system, comprising:
a vehicle component;
an electrocardiography (ECG) sensor for sensing a current ECG information;
a first register for storing the current ECG information;
a remote controller, comprising:
a second register for storing a pre-recorded ECG information;

a microcontroller for controlling the vehicle component change to a second state from a first state if the current ECG information matches the pre-recorded ECG information, wherein the first state is different from the second state; and a MEMS sensor for sensing whether the remote controller leaves a user.

2. The vehicle burglarproof system according to claim 1, further comprising:

an indication device, wherein if the current ECG information does not match the pre-recorded ECG information, the microcontroller outputs an error message to the indication device and determines whether the current ECG information needs to be verified once again.

3. The vehicle burglarproof system according to claim 2, further comprising:

a control key, wherein after the control key is activated, the microcontroller determines whether the current ECG information exists, and if the current ECG information does not exist, the microcontroller outputs a current ECG information request to the indication device.

4. The vehicle burglarproof system according to claim 3, wherein if the current ECG information exists and the remote controller does not leave the user, the microcontroller controls the vehicle component to change to the second state from the first state.

5. The vehicle burglarproof system according to claim 4, wherein if the remote controller leaves the user, the microcontroller once again determines whether the current ECG information exists.

6. The vehicle burglarproof system according to claim 3, wherein the control key is an unlocking button.

7. The vehicle burglarproof system according to claim 6, wherein the vehicle component is a burglarproof device, the first state is a locking state, and the second state is an unlocking state.

8. The vehicle burglarproof system according to claim 3, wherein the control key is a start button.

9. The vehicle burglarproof system according to claim 8, wherein the vehicle component is an engine, the first state is an engine non-activated state, and the second state is an engine activated state.

10. The vehicle burglarproof system according to claim 2, wherein the indication device is a light emitting diode (LED) disposed on the remote controller.

11. The vehicle burglarproof system according to claim 2, wherein the indication device is a dashboard.

12. A vehicle burglarproof method, comprising:

sensing a current ECG information;

determining whether the current ECG information matches a pre-recorded ECG information stored in a remote controller;

sensing and determining whether the remote controller leaves a user; and controlling a vehicle component change to a second state from a first state if the current ECG information matches the pre-recorded ECG information, wherein the first state is different from the second state.

13. The vehicle burglarproof method according to claim 12, further comprising:

outputting an error message and determining whether the current ECG information needs to be verified once again if the current ECG information does not match the pre-recorded ECG information.

14. The vehicle burglarproof method according to claim 12, further comprising:

determining whether the current ECG information exists after a control key is activated; and outputting a current ECG information request if the current ECG information does not exist.

15. The vehicle burglarproof method according to claim 14, further comprising:

controlling the vehicle component to change to the second state from the first state if the current ECG information exists and the remote controller does not leave the user.

16. The vehicle burglarproof method according to claim 15, wherein if the remote controller leaves the user, determining whether the current ECG information exists once again.

17. The vehicle burglarproof method according to claim 14, wherein the control key is an unlocking button.

18. The vehicle burglarproof method according to claim 17, wherein the vehicle component is a burglarproof device, the first state is a locking state, and the second state is an unlocking state.

19. The vehicle burglarproof method according to claim 14, wherein the control key is a start button.

20. The vehicle burglarproof method according to claim 19, wherein the vehicle component is an engine, the first state is an engine non-activated state, and the second state is an engine activated state.

* * * * *